(12) United States Patent
Hasegawa et al.

(10) Patent No.: US 7,833,162 B2
(45) Date of Patent: Nov. 16, 2010

(54) ULTRASONIC PROBE

(75) Inventors: Shigeyoshi Hasegawa, Tsukui-gun (JP); Kazuyoshi Irioka, Sagamihara (JP); Jun Koizumi, Yokohama (JP); Michiyo Hirayama, Chigasaki (JP)

(73) Assignee: Panasonic Corporation, Osaka (JP)

( * ) Notice: Subject to any disclaimer, the term of this patent is extended or adjusted under 35 U.S.C. 154(b) by 1083 days.

(21) Appl. No.: 10/511,478

(22) PCT Filed: Apr. 15, 2003

(86) PCT No.: PCT/JP03/04740

§ 371 (c)(1),
(2), (4) Date: Oct. 15, 2004

(87) PCT Pub. No.: WO03/088705

PCT Pub. Date: Oct. 23, 2003

(65) Prior Publication Data

US 2005/0184624 A1 Aug. 25, 2005

(30) Foreign Application Priority Data

Apr. 17, 2002 (JP) .............................. 2002-115355

(51) Int. Cl.
*A61B 8/14* (2006.01)
(52) U.S. Cl. ...................... 600/459; 600/462
(58) Field of Classification Search ................ 600/459, 600/407, 437, 462
See application file for complete search history.

(56) References Cited

U.S. PATENT DOCUMENTS

| 4,517,985 A | | 5/1985 | Teslawski et al. | |
| 4,967,753 A | | 11/1990 | Haase et al. | |
| 5,469,853 A | * | 11/1995 | Law et al. | 600/463 |
| 5,550,790 A | | 8/1996 | Velamoor et al. | |
| 5,640,961 A | * | 6/1997 | Verdonk | 600/459 |
| 5,715,825 A | * | 2/1998 | Crowley | 600/462 |
| 5,762,066 A | | 6/1998 | Law et al. | |
| 5,897,504 A | * | 4/1999 | Buck et al. | 600/463 |
| 5,997,481 A | * | 12/1999 | Adams et al. | 600/459 |
| 6,468,220 B1 | * | 10/2002 | Elasri et al. | 600/459 |

FOREIGN PATENT DOCUMENTS

| DE | 197 42 294 | | 4/1999 |
| EP | 0 286 359 | | 10/1988 |
| JP | 56-116008 | | 9/1981 |
| JP | 61-119249 | | 6/1986 |
| JP | 2-98341 | | 4/1990 |
| JP | 2098341 A2 | * | 4/1990 |
| JP | 2-189139 | | 7/1990 |
| JP | 3-131278 | | 6/1991 |

(Continued)

*Primary Examiner*—Brian Casler
*Assistant Examiner*—Peter Luong
(74) *Attorney, Agent, or Firm*—Hamre, Schumann, Mueller & Larson, P.C.

(57) ABSTRACT

An ultrasonic probe, including an ultrasonic element for transmitting and receiving ultrasonic waves; a sound window enclosing the ultrasonic element; and a sound propagation liquid charged in the sound window. A barrier layer capable of inhibiting the permeation of liquids and gases is provided on a wall surface of the sound window. As the barrier layer, at least one selected from a polyparaxylylene layer and a metal layer can be used.

7 Claims, 3 Drawing Sheets

FOREIGN PATENT DOCUMENTS

| | | |
|---|---|---|
| JP | 3-289950 | 12/1991 |
| JP | 6-209937 | 8/1994 |
| JP | 6209937 A2 * | 8/1994 |
| JP | 10-262974 | 10/1998 |
| JP | 11-285496 | 10/1999 |
| JP | 2002078673 A * | 3/2002 |

* cited by examiner

ULTRASONIC PROBE

TECHNICAL FIELD

The present invention relates to an ultrasonic probe. More specifically, it relates to an ultrasonic probe comprising an ultrasonic element, a sound window enclosing the ultrasonic element and a sound propagation liquid charged in the sound window.

BACKGROUND ART

An ultrasonic probe is used for a fish finder, an ultrasonic diagnostic equipment used with living bodies, or the like. As the ultrasonic equipment used for an ultrasonic diagnostic equipment, an ultrasonic probe including an ultrasonic element for transmitting and receiving ultrasonic waves, a sound window enclosing the ultrasonic element and a sound propagation liquid having a sound impedance, which is approximate to that of a living body, charged in the sound window is well known (see, for example, JP02 (1990)-98341 A).

Such ultrasonic probes use a resin for a material that constitutes the sound window, from the viewpoint of the sound properties. Therefore, since the water absorption rate is different depending upon the used resins due to the influence of the molecular structure, etc., after a long time of use, depending upon the kinds, temperature and resin materials, etc., of the sound propagation liquid, the sound propagation liquid may intrude into a resin that constitutes the sound window, or further may penetrate the sound window and leak toward the outside. As a result, the pressure inside the sound window is lowered so as to become lower than the external pressure, so that an air may penetrate the resin that constitutes the sound window and the air may be a contaminant inside the sound window. When air bubble contaminates into the sound window, it acts as a reflector with respect to the ultrasonic waves, thus inhibiting the transmittance and receiving of the ultrasonic waves, which in turn may lead to the deterioration of ultrasonic diagnostic images. In order to suppress an occurrence of such air bubbles, in this kind of ultrasonic probes, a sound propagation liquid has to be refilled over time so as to maintain the pressure inside the sound window.

SUMMARY OF THE INVENTION

With the foregoing in mind, it is therefore an object of the present invention to provide an ultrasonic probe capable of suppressing the permeation of the sound propagation liquid from the sound window and maintaining the pressure inside the sound window.

In order to achieve the above-mentioned object, the ultrasonic probe of the present invention includes an ultrasonic element made of piezoelectric substance for transmitting and receiving ultrasonic waves, a sound window enclosing the element and an ultrasonic wave propagation liquid charged in the sound window, wherein the sound window is provided with a barrier layer capable of inhibiting the permeation of liquids and gases.

For the above-mentioned barrier layer, for example, a layer including at least one of a polyparaxylylene layer and a metal layer can be used.

BEST MODE FOR CARRYING OUT THE INVENTION

Figure 1:
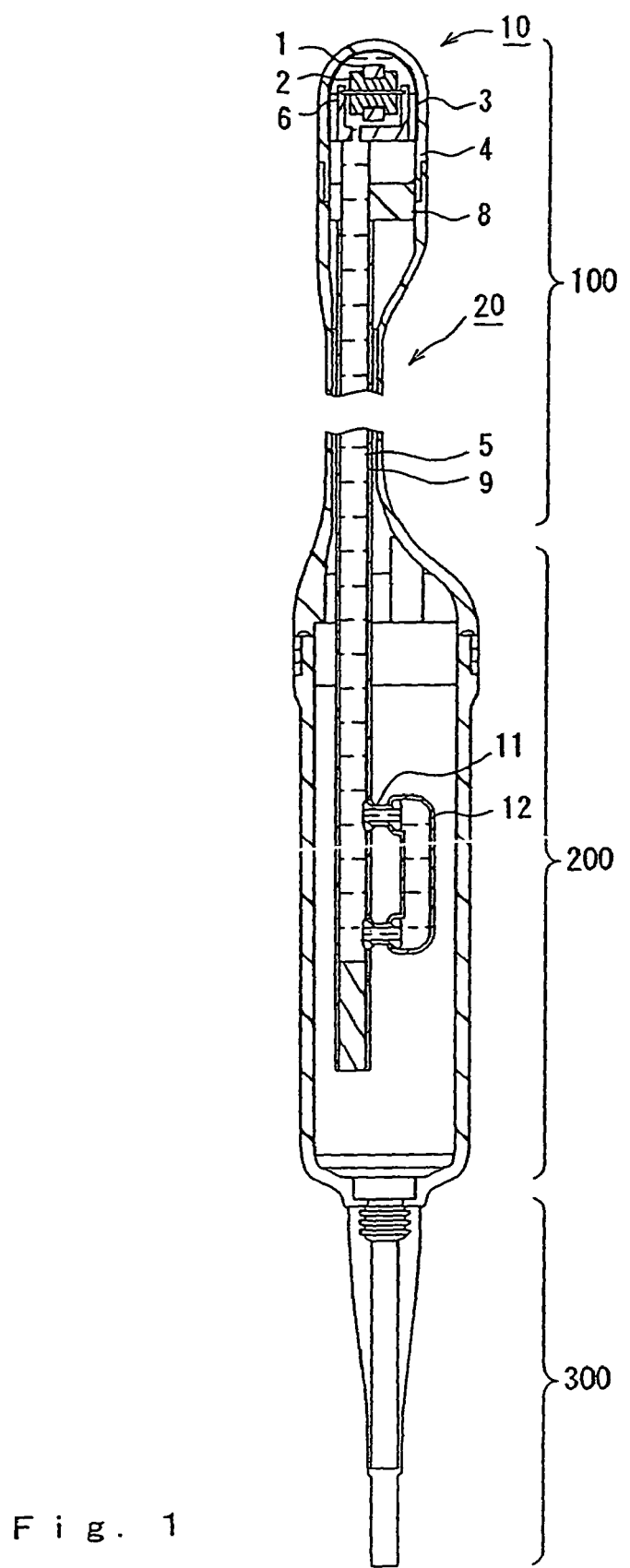
FIG. 1 is a schematic cross-sectional view showing one example of an ultrasonic probe of the present invention.

As mentioned above, the ultrasonic probe of the present invention includes an ultrasonic element for transmitting and receiving ultrasonic waves, a sound window enclosing the ultrasonic element and an ultrasonic wave propagation liquid charged in the sound window. In the sound window, a barrier layer capable of inhibiting the permeation of liquids and gases is formed. With such a configuration, it is possible to suppress the permeation of the sound propagation liquids from the sound window and to suppress the reduction of the amount of liquids. As a result, the pressure in the sound window can be maintained.

It is preferable that the barrier layer is formed on an internal wall surface of the sound window.

As the barrier layer, polyparaxylylene or the derivative thereof can be used. As the polyparaxylylene derivative, polyparaxylylene with each aromatic ring having at least one hydrogen substituted with, for example, chlorine, bromine, fluorine, an alkyl group, an amino group, etc. can be used. The layer thickness of the polyparaxylylene layer is preferably in the range from 0.1 μm to 500 μm and more preferably 1 μm to 100 μm because the inhibiting property is excellent and the film formation is easy.

The polyparaxylylene layer can be formed as a polyparaxylylene resin layer by a chemical vapor deposition of diparaxylylene or the derivative thereof. As diparaxylylene, for example, "Parylene" manufactured by Three Bond Co., Ltd. can be employed. Furthermore, as the diparaxylylene derivative, diparaxylylene with each aromatic ring having at least one hydrogen substituted with, for example, chlorine, bromine, fluorine, an alkyl group, an amino group, etc. can be used.

One example of the method for forming this polyparaxylylene resin layer will be described in more detail. This resin can be made radical by firstly thermal decomposing paraxylene at about 900° C. as shown in the following chemical formula [Formula 1] in the presence of water, and quenched in benzene or toluene at 50° C. to 250° C. Thus, diparaxylene that is a cyclic dimer can be obtained.

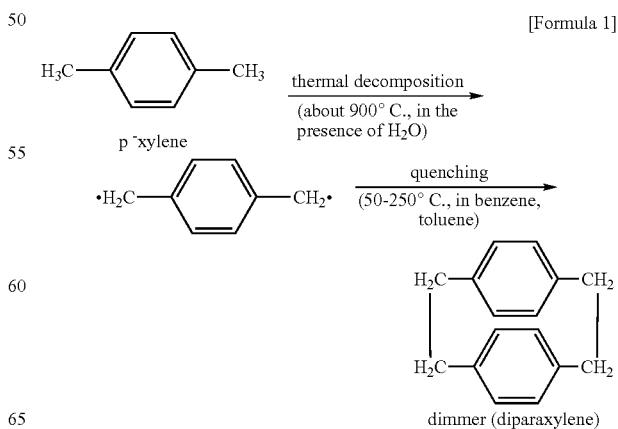

[Formula 1]

The obtained diparaxylene is heated about 600° C. under low pressure so as to be thermally decomposed and formed into a paraxylylene radical gas intermediate. This gas is extremely reactive. When this gas is introduced to the internal wall surface of the sound window, it is condensed and polymerized. Thus, a layer form of polyparaxylylene is obtained. The molecular weight of this polyparaxylylene is about 500,000. Note here that in Formula 2, n denotes a repeating unit.

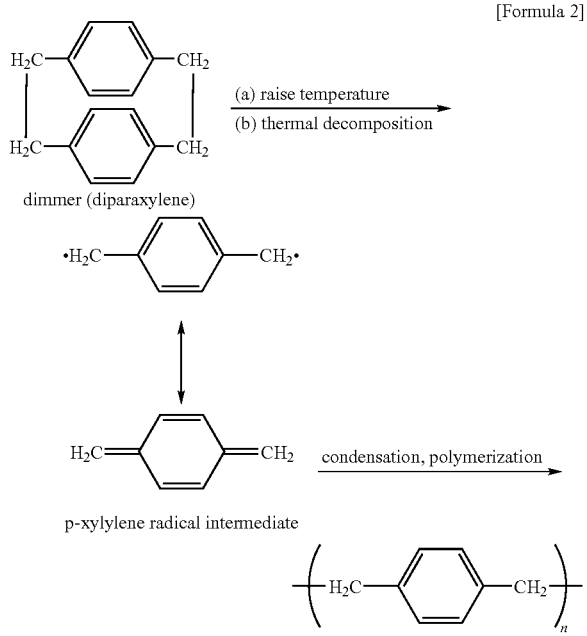

[Formula 2]

Thus, the polyparaxylylene layer can be formed by vapor-depositing diparaxylene or the derivative thereof. The vapor deposition rate is generally in the range from 0.01 μm/min to 0.2 μm/min. According to the method using this vapor deposition process, an extremely thin layer can be formed and it is possible to prevent the sound propagation liquids from permeating and flowing out.

As the barrier layer, a metal layer may be used. In this case, the metal layer may use a metal such as aluminum, gold, nickel, platinum, etc. Preferably, a metal such as aluminum and gold can be used. Furthermore, the layer thickness of the metal layer is preferably 0.1 μm to 30 μn because an excellent property of inhibiting liquid permeation is provided and the film formation is easy.

The metal layer can be formed by, for example, a vapor deposition method. Furthermore, the metal layer may be formed by an attachment of a metal thin film. Thus, it is possible to form a thin film layer and to prevent the sound propagation liquid from permeating and flowing out.

Hereinafter, the present invention will be described by way of a preferable embodiment and with reference to drawings.

FIG. 1 is a cross-sectional view showing one example of a structure of the ultrasonic probe according to the present invention. This ultrasonic probe is an intracorporeal insertion type probe used for an ultrasonic diagnosis. A part of this probe is inserted into the body cavity of a subject and ultrasonic scanning is carried out in the body cavity. This ultrasonic probe includes an inserting portion 100 to be inserted into the body cavity and a grip portion 200 held by an operator outside of the body.

Figure 2:
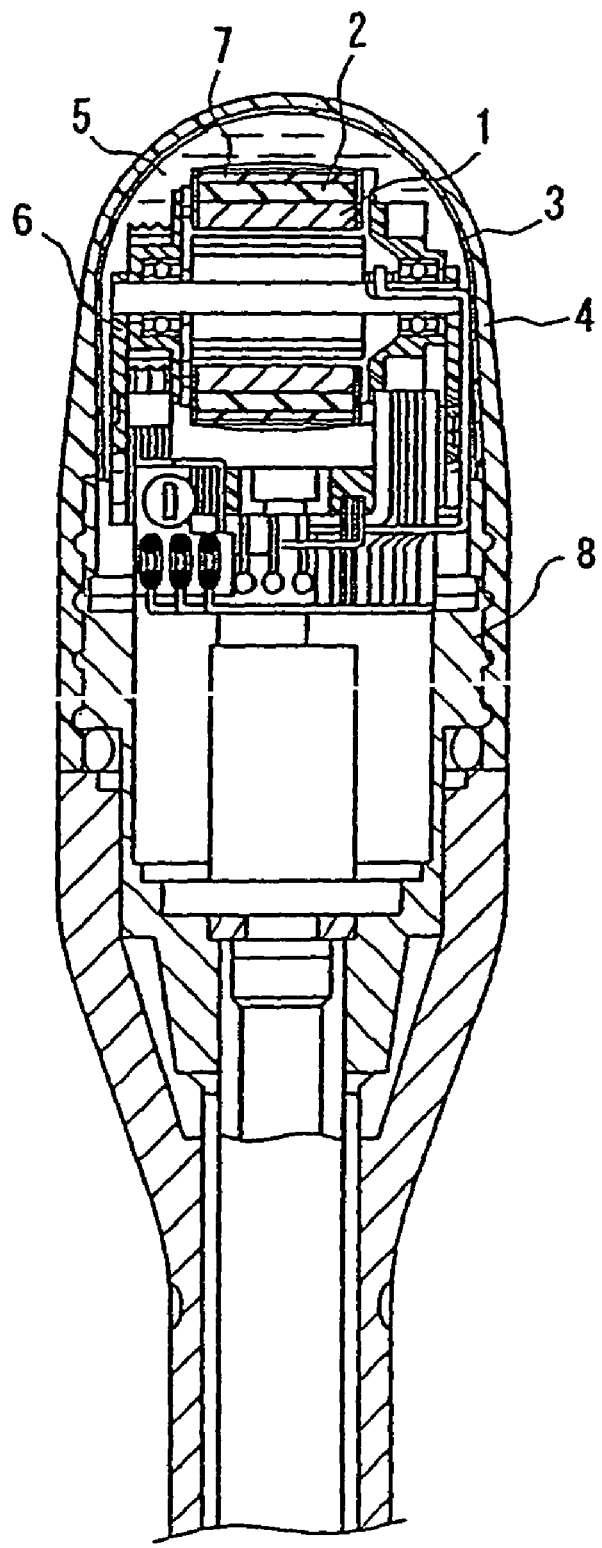
FIG. 2 is an enlarged cross-sectional view showing a storage portion of the above-mentioned ultrasonic probe.

The insertion portion 100 includes a storage portion 10 disposed at the tip portion thereof; and a rod portion 20 for locating the storage portion 10 at the desirable portion in the body cavity. The storage portion 10 is constructed in a way in which a sound window 4 and a frame 8 are connected. Inside the storage portion 10, an ultrasonic element unit is stored. Note here that in FIG. 1, for simplification, the interior structure of the storage portion 10 is simplified. FIG. 2 is an enlarged cross-sectional view showing a detailed interior structure of the storage portion 10.

The sound window 4 is not particularly limited. Those conventionally used may be used. However, it is preferable to use poly(methyl pentene-1) having a thickness of about 1 to 3 mm. It is advantageous because with this thickness, it is possible to avoid distortion of the extracted image since the sound window 4 is less distorted when it is pushed toward the body surface and because this thickness permits the ultrasonic attenuation.

Figure 3:
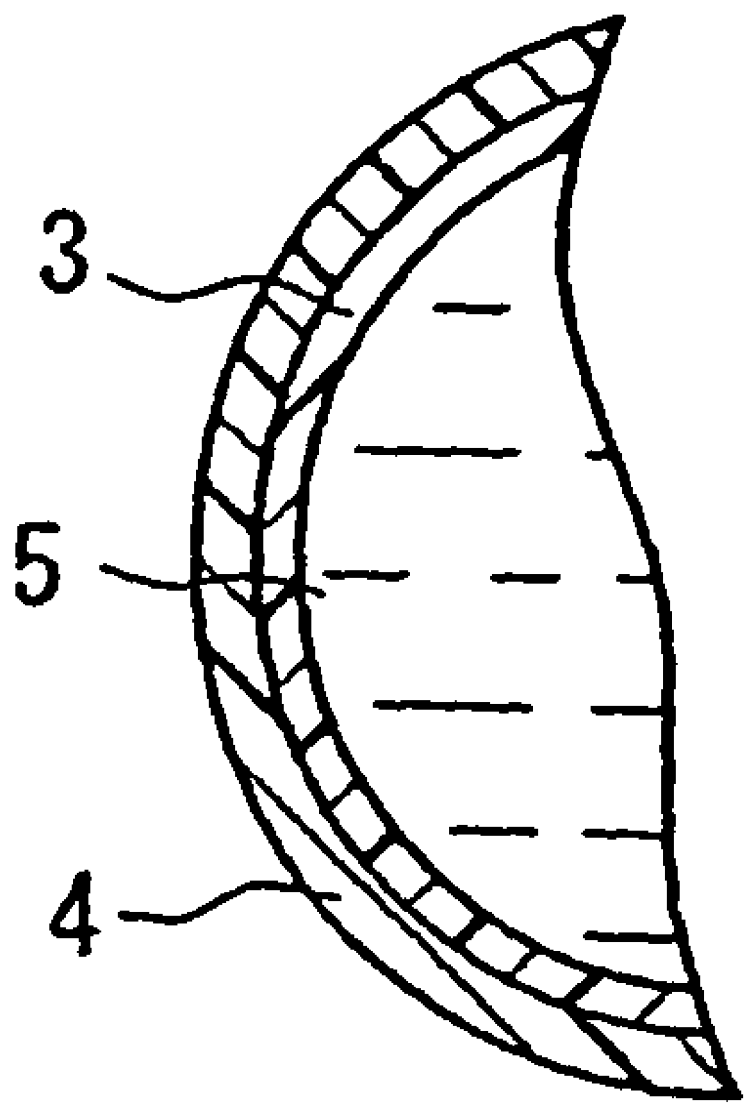
FIG. 3 is an enlarged cross-sectional view showing a sound window of the above-mentioned ultrasonic probe.

As mentioned above, on the internal wall surface of the sound window 4, a barrier layer 3 is formed. As shown in FIG. 3, it is preferable that the barrier layer 3 is formed in close contact with the internal wall surface of the sound window 4. When such a sound window 4 having the barrier layer 3 is used in the ordinary room environment, since the reduction of liquid amount due to the permeation of liquids is extremely small and little drop in the internal pressure occurs, a stable shape can be secured. In this embodiment, the barrier layer 3 is a polyparaxylylene layer having a thickness of 5 μm. This polyparaxylylene layer, as mentioned above, can be formed efficiently, for example, by vapor-depositing "Parylene" (a product manufactured by Three Bond Co., Ltd.). Furthermore, in a case where the film thickness of the polyparaxylylene layer is thick, or the window has a simple shape, an attachment method can be employed. Furthermore, as the barrier layer 3, a vapor-deposited film or attached film made of aluminum, gold, etc. can also be used.

Inside the sound window 4 of the storage portion 10, a degassed sound propagation liquid 5 is charged. As the sound propagation liquid 5, for example, physiological saline can be used. Furthermore, a frame 8 is provided with a through hole to which a pipe 9 is linked. The pipe 9 extends toward the grip portion 200 by way of a rod portion 20. The sound propagation liquid 5 also is charged in this pipe 9. Thus, the inside of the sound window 4 is configured so that the sound propagation liquid 5 is in communication to a reserve tank 12 via this pipe 9. The reserve tank 12 will be described later.

The ultrasonic element unit includes an oscillator 2 and a rotation mechanism portion for holding and rotating the oscillator 2. Furthermore, a surface for transmitting and receiving ultrasonic waves of the oscillator 2 is provided with a sound lens 7. The rotation mechanism portion may be, for example, a spontaneous rotation type motor and includes a rotor 1 on which the oscillator 2 is mounted, a bracket 6 that rotatably supports this rotor and a rotation driving source (magnet) for providing the rotor 1 with a rotation power. Such a rotation mechanism portion allows the oscillator 2 to rotate along with the rotation of the rotor 1. Thus, it is possible to realize mechanical scanning with a circular orbit of the ultrasonic waves. Furthermore, from the ultrasonic element unit, a plurality of signal lines for transmitting and receiving electric signals for driving the oscillator 2 and the rotation mechanism portion are led out. These lead lines are introduced into the grip portion 200 via the rod portion 20.

The grip portion 200 contains a reserve tank 12 in which the sound propagation liquid 5 is charged. This reserve tank 12 absorbs the change in the internal pressure inside the sound window 4 due to the temperature change and maintains the operation pressure. This reserve tank 12 is linked to the pipe 9 via a nozzle 11 and configured so that the sound propagation liquid 5 is in communication to the sound window 4. The reserve tank 12 is formed of an elastic container capable of altering its volume in accordance with the charged amount when liquids are charged in the container.

In this embodiment, preferably, also on the wall surface of the reserve tank 12, similar to the sound window 4, a barrier layer is formed. Furthermore, preferably, also on the wall surface of the pipe 9 connecting the storage portion 10 and the reserve tank 12, similarly, a barrier layer is formed.

Furthermore, from the grip portion 200, a cable 300 is led out. The ultrasonic probe is connected to the ultrasonic diagnostic equipment via this cable 300.

Next, an operation of the above-mentioned ultrasonic probe will be described.

First of all, in the vicinity of a subject, an ultrasonic probe is located so as to drive a rotation mechanism portion and to rotate the rotor 1. Thereby, the oscillator 2 mounted on the rotor 1 starts rotational movement. Next, electric signals (transmitted signals) from the ultrasonic diagnostic equipment are transmitted to the oscillator 2. These transmitted signals are converted into ultrasonic waves and propagate in the sound propagation liquid 5, permeate the sound window 4 and are transmitted to the subject. These ultrasonic waves are reflected from the subject. A part of the reflected waves are received by the oscillator 2 and converted into ultrasonic signals (received signal) and sent to the ultrasonic diagnostic equipment. The received signals are converted into image data in the ultrasonic diagnostic equipment. By carrying out this operation for transmitting and receiving ultrasonic waves while rotating repeatedly, scanning of the ultrasonic waves can be carried out.

According to this embodiment, by providing the barrier layer 3 on the internal surface of the sound window 4, it is possible to suppress filtration or permeation of the sound propagation liquid 5 into the sound window 4 and to decrease the change in pressure of the sound propagation liquid 5. Therefore, the change in the internal pressure inside the sound window 4 can be reduced and the shape thereof can be maintained. Furthermore, since a sufficient amount of sound propagation liquid 5 is always charged, propagation of ultrasonic waves can be carried out with high fidelity.

Note here that in the above description, the barrier layer 3 is provided on the internal wall surface of the sound window 4. However, the barrier layer 3 may be provided on the external surface of the sound window. Alternatively, in the case of the sound window configured of a plurality of layers, the same effect can be obtained if the barrier layer 3 is provided between layers. In this case, in order to improve the adhesion between the layers constituting the window, a part of the barrier layer may be provided with a through hole.

Furthermore, in the description, an example of the mechanical scanning in which the oscillator is rotated by a motor is described. The mechanical scanning method by the array type element in which a plurality of oscillators are arranged may be employed.

Furthermore, an example in which the barrier layer is formed of a polyparaxylylene layer or a metal layer is described, the barrier layer may be formed of a multilayer including a polyparaxylylene layer and a metal layer. Furthermore, because the permeation rate of the sound propagation liquid through resin varies depending upon the type of the sound propagation liquid, the other film having a property corresponding to the type of sound propagation liquid may be provided.

INDUSTRIAL APPLICABILITY

As mentioned above, according to the ultrasonic probe of the present invention, by providing a barrier layer on the internal wall of the sound window, it is possible to provide an ultrasonic probe in which filtration and permeation of the sound propagation liquids to materials of the sound window. Such ultrasonic probes can be used for, for example, an ultrasonic diagnostic equipment, and the like.

The invention claimed is:

1. An ultrasonic probe, comprising:
a probe chassis comprising an insertion portion and a grip portion formed integrally with each other;
an ultrasonic element for transmitting and receiving ultrasonic waves, which is disposed at the tip portion of the insertion portion;
a sound window formed of the probe chassis at the insertion portion, enclosing the ultrasonic element;
a barrier layer on an internal wall surface of the sound window;
a pipe disposed inside the probe chassis from the insertion portion to the grip portion, in communication to an area enclosed by the sound window;
an elastic reserve tank having a wall disposed inside the probe chassis at the grip portion, in communication with the pipe; and
a charged sound propagation liquid in an area enclosed by the sound window, in the pipe and inside the elastic reserve tank;
wherein the wall of the elastic reserve tank is separate from the internal wall of the probe chassis at the grip portion; and
the elastic reserve tank absorbs changes of pressure of the charged sound propagation liquid in the area enclosed by the sound window to maintain the pressure within and shape of the sound window.

2. The ultrasonic probe according to claim 1, wherein the barrier layer comprises at least one selected from a polyparaxylylene layer and a metal layer.

3. The ultrasonic probe according to claim 2, wherein the barrier layer comprises a polyparaxylylene layer and the layer thickness of the polyparaxylylene layer is in the range from 0.1 µm to 500 µm.

4. The ultrasonic probe according to claim 2, wherein the barrier layer comprises a polyparaxylylene layer formed by a chemical vapor deposition of diparaxylylene or a derivative thereof.

5. The ultrasonic probe according to claim 2, wherein the barrier layer comprises a metal layer and the metal layer comprises at least one selected from the group consisting of aluminum, gold, nickel and platinum.

6. The ultrasonic probe according to claim 2, wherein the barrier layer comprises a metal layer and the thickness of the metal layer is in the range from 0.1 µm to 30 µm.

7. The ultrasonic probe according to claim 2, wherein the barrier layer comprises a plurality of layers.

* * * * *